United States Patent
Sato et al.

[11] Patent Number: 5,966,195
[45] Date of Patent: Oct. 12, 1999

[54] METHOD OF DETERMINING CELL THICKNESS AND TWIST ANGLE PARAMETERS OF LIQUID CRYSTAL CELL

[75] Inventors: Susumu Sato; Ying Zhou; Zhan He, all of Akita; Yoshihiro Togashi, Kasugai, all of Japan

[73] Assignee: Meiryo Tekunika Kabushiki Kaisha, Japan

[21] Appl. No.: 08/974,994

[22] Filed: Nov. 20, 1997

[30] Foreign Application Priority Data

Nov. 25, 1996 [JP] Japan ................................ 8-313720

[51] Int. Cl.$^6$ ................ G02F 1/13; G01J 4/00; G02B 11/06
[52] U.S. Cl. ..................... 349/187; 356/367; 356/382; 356/364
[58] Field of Search ................. 349/113, 187; 356/364, 367, 359, 365, 366, 368; 324/770

[56] References Cited

U.S. PATENT DOCUMENTS

| | | | |
|---|---|---|---|
| 5,239,365 | 8/1993 | Inoue | 356/367 |
| 5,298,972 | 3/1994 | Heffner | 356/364 |
| 5,532,823 | 7/1996 | Fukui et al. | 356/364 |
| 5,691,791 | 11/1997 | Nakamura et al. | 349/113 |

FOREIGN PATENT DOCUMENTS

| | | |
|---|---|---|
| 6-289382 | 10/1984 | Japan . |
| 63-103925 | 5/1988 | Japan . |
| 63-103927 | 5/1988 | Japan . |
| 2-103427 | 4/1990 | Japan . |
| 5-172644 | 7/1993 | Japan . |
| 6-18332 | 1/1994 | Japan . |
| WO8607631 | 12/1986 | WIPO . |

OTHER PUBLICATIONS

"Cell Gap Measurement—Compensation Method" printed in J. Appln. Phys. 69(3) published on Feb. 1, 1991.

"A New Method—Liquid Crystal" printed in Jpn. J. Appln. Phys. vol. 33 published on Mar. 15, 1994.

"Method of Studying—Liquid Crystal" printed in Jpn. J. Appln. Phys. vol. 33 published on Sep. 1, 1994.

"Novel Method—Liquid Crystal" printed in Jpn. J. Appln. Phys. vol. 35 published in Aug., 1996.

"The Evaluation of the Torsional Anchoring Energy of TN–cells" published at 22th Liquid Crystal Conference 1996 (No. 22 Ekisho Toronkai).

Yamauchi, Makoto "Optimization of twisted nematic liquid crystal panels for spatial light phase modulation" Optics Communications 115, pp. 19–25, Mar. 1995.

Tang, S.T. and Kwok, H.S. "A New Method for Liquid Crystal Cells Twist Angle and Cell Gap Measurement".

Primary Examiner—William L. Sikes
Assistant Examiner—Kari M. Horney
Attorney, Agent, or Firm—Douglas J. Christensen

[57] ABSTRACT

A method of determining a parameter of a liquid crystal cell is provided in which parameters, such as the thickness of the liquid crystal layer and the angle of the twist of liquid crystal molecule orientation in the liquid crystal cell, are accurately determined in a short time with a simple apparatus. Light from a light source 1 is transmitted through a polarizing plate 2 and incident to a liquid crystal cell 3. The light is transmitted by a polarizing plate 4 and the intensity of the transmitted light is measured by a photodetector 6. Then, the outputs of the photodetector 6 for the following cases are measured: when the polarization direction of the polarizing plate 4 is set (1) in the direction of the X axis, (2) in the direction of Y axis and (3) at 45 degrees to the X and Y axes and (4) when, with the polarization direction of the polarizing plate 4 being at 45 degrees to the X and Y axes, a quarter wavelength plate 5 is inserted between the polarizing plate 4 and the liquid crystal cell 3 so that its axial direction is tilted at 45 degrees to the polarization direction of the polarizing plate 4. Stokes parameters are obtained from the measurement values, and the thickness of the liquid crystal layer and the angle of twist of liquid crystal molecule orientation are calculated from the measured Stokes parameters.

20 Claims, 3 Drawing Sheets

| SAMPLE | SETTING | | MEASUREMENT | |
|---|---|---|---|---|
| | THICKNESS OF LIQUID CRYSTAL LAYER | ANGLE OF TWIST | THICKNESS OF LIQUID CRYSTAL LAYER | ANGLE OF TWIST |
| SAMPLE 1 | 25 μm | 30° | 25.32 μm | 29.79° |
| SAMPLE 2 | 25 μm | 85° | 24.85 μm | 85.97° |
| SAMPLE 3 | 5 μm | 85° | 4.87 μm | 83.85° |

FIG. 5

METHOD OF DETERMINING CELL THICKNESS AND TWIST ANGLE PARAMETERS OF LIQUID CRYSTAL CELL

BACKGROUND OF THE INVENTION

1. Field of the Invention

The present invention relates to a method of detecting parameters, particularly, the thickness of the liquid crystal layer and the angle of twist of liquid crystal molecule orientation, of a liquid crystal cell for use in a liquid crystal display and the like.

2. Description of the Prior Art

In liquid crystal cells, all of the liquid crystal molecules are oriented parallel to the plane of the two substrates and the direction of orientation is gradually twisted between the two substrates. Examples of such liquid crystal cells include a twisted nematic liquid crystal cell (hereinafter referred to as "TN cell") in which the direction of orientation is twisted exactly 90 degrees and a super twisted nematic liquid crystal cell (hereinafter referred to as "STN cell") in which the direction of orientation is twisted between 180 degrees and 270 degrees. These liquid crystal cells are widely used in various liquid crystal displays such as displays for word processors and personal computers.

In such TN and STN cells, the display quality greatly depends on the distance between the two substrates, i.e. the thickness of the liquid crystal layer, and the angle of twist of the liquid crystal molecule orientation.

The anchoring energy (i.e., the orientation restriction force in the direction of azimuth on the liquid crystal cell substrate plane), which is one of the important parameters of liquid crystal cells, can be obtained from a variation of angle of twist of the liquid crystal molecule orientation between the two substrates.

Therefore, in the manufacture of liquid crystal cells, it is extremely important to quickly and accurately detect the thickness of the liquid crystal layer and the angle of twist of the liquid crystal molecule orientation.

Conventionally known methods for determining the thickness of a liquid crystal layer include (1) a method in which capacitance and optical phase difference of the liquid crystal cell are measured to thereby calculate the thickness of the liquid crystal layer, (2) a method in which light interference and capacitance are measured in an empty cell state, i.e., where no liquid crystal has been sealed in yet, to thereby calculate the thickness of the liquid crystal layer, and (3) a method in which the distance between the two substrates is measured by use of a three-dimensional shape measuring method to thereby calculate the thickness of the liquid crystal layer.

Known methods for determining the angle of twist of liquid crystal molecule orientation include a method in which (1) a liquid crystal cell is interposed between two polarizing plates, (2) the optical path difference is adjusted by a photoelastic modulation element and (3) curve fitting of the transmitted light intensity is performed, thereby determining the angle of twist of liquid crystal molecule orientation.

Moreover, a method is known in which (1) a liquid crystal cell is interposed between two polarizing plates, (2) one or both of the liquid crystal cells and the polarizing plates are rotated to thereby obtain an angle in which the transmitted light intensity is at a maximum or minimum, and (3) the thickness of the liquid crystal layer and the angle of twist of liquid crystal molecule orientation are obtained by use of a Jones' matrix display.

These methods are described in "J. Appl. Phys." (vol. 69, p.1304), "Jpn. J. Appl. Phys." (vol. 33, pp. L434–L436), "Jpn. J. Appl. Phys." (vol. 33, pp. L1242–L1244), "Jpn. J. Appl. Phys." (vol. 35, pp. 4434–4437) and "Manuscripts of Lectures at the 22nd Japanese Liquid Crystal Conference" (pp. 139–140), etc.

However, according to the conventional methods, it is difficult to accurately determine the thickness of the liquid crystal layer because the capacitance and the optical difference of the liquid crystal cell are measured. In addition, the apparatus is complicated and expensive since an optical path difference modulation element such as a photoelastic modulation element and a phase compensation element is necessary. Further, the apparatus is complicated and expensive and errors are apt to be caused since curve fitting of the transmitted light intensity is performed or the polarizing plates and the liquid crystal cell are rotated to measure an angle where the transmitted light intensity is maximum or minimum.

To overcome the above-mentioned problems, the inventors performed various studies and found that the thickness of the liquid crystal layer and the angle of liquid crystal molecule orientation can be obtained based upon Stokes parameters and that the Stokes parameters can be accurately measured in a short time with a simple apparatus.

SUMMARY OF THE INVENTION

An object of the present invention is to provide a method of detecting a parameter of a liquid crystal cell wherein a liquid crystal cell parameter such as the thickness of the liquid crystal layer or the angle of the twist of a liquid crystal molecule orientation is accurately determined in a short time with a simple apparatus.

To achieve the above-mentioned objects in the invention according to claim 1, a Stokes parameter of a liquid crystal cell in which liquid crystal material is sandwiched between two substrates is measured, and at least one of a thickness of a liquid crystal layer and an angle of the twist of liquid crystal molecule orientation between the substrates is obtained based on the measured Stokes parameter.

By using the method of detecting a parameter of a liquid crystal cell according to claim 1, the thickness of the liquid crystal layer and/or the angle of twist of liquid crystal molecule orientation can be accurately determined in a short time with a simple apparatus.

BRIEF DESCRIPTION OF THE DRAWINGS

FIG. 5 is a table showing data for liquid crystal cell parameters for a plurality of liquid crystal cells calculated using the liquid crystal cell parameter detecting method of the present invention.

DETAILED DESCRIPTION OF THE PREFERRED EMBODIMENTS

An embodiment of a liquid crystal cell parameter determining method according to the present invention will hereinafter be described with reference to the drawings.

Figure 1:
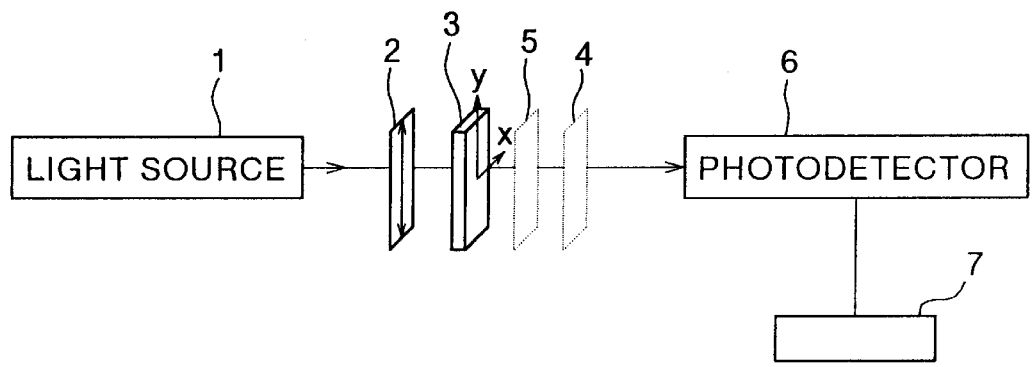
FIG. 1 is a structural view of an embodiment of a liquid crystal cell parameter detecting apparatus for performing a liquid crystal cell parameter detecting method according to the present invention.

FIG. 1 is a schematic structural view of an embodiment of a liquid crystal cell parameter detecting apparatus for performing the liquid crystal cell parameter detecting method of the present invention.

In FIG. 1, reference numeral 1 represents a light source which may be, for example, a He-Ne laser with a wavelength of 632.8 nm. Light from the light source 1 is applied along the Z axis of the apparatus.

Reference numeral 2 represents a polarizing plate (polarizer) whose direction of polarization is set in the direction of the Y axis.

Reference numeral 3 represents a liquid crystal cell such as a TN cell or an STN cell.

Reference numeral 4 represents a polarizing plate (analyzer) whose direction of polarization is settable (1) in the direction of the X axis, (2) in the direction of the Y axis and (3) at 45 degrees to the X and Y axes.

Reference numeral 5 represents a quarter wavelength plate which may be inserted between the liquid crystal cell 3 and the polarizing plate 4 with its axial direction being tilted at 45 degrees to the polarization direction of the polarizing plate 4.

Reference numeral 6 represents a photodetector, such as a photodiode, which measures the intensity of light transmitted by the polarizing plate 4 and outputs a transmitted light intensity signal.

Reference numeral 7 is a processor, such as a personal computer, for processing data which processor calculates (1) Stokes parameters of the liquid crystal cell 3, (2) the thickness of the liquid crystal layer and (3) the angle of the twist of liquid crystal molecule orientation based on the transmitted light intensity signal outputted from the photodetector 6.

A basic principle of the liquid crystal cell parameter detecting method according to the present invention will be described now.

Figure 2:
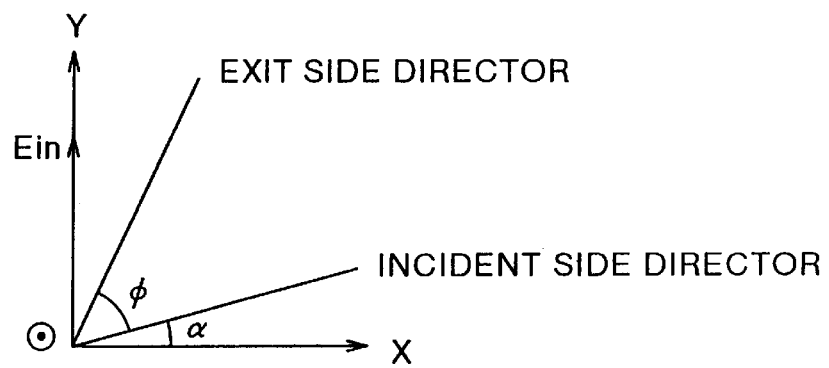
FIG. 2 is a view showing the direction of polarization of incident light, the direction of orientation (direction of director) of liquid crystal molecules and the angle of the twist of liquid crystal molecule orientation.

A coordinate system as shown in FIG. 2 is provided for use with this method.

In the coordinate system shown in FIG. 2, the polarization direction of the incident side polarizing plate 2 is the direction of the Y axis.

The angle between the X axis and the director of the light incident side liquid crystal of the liquid crystal cell 3 is identified as "$\alpha$" and the angle of twist of the liquid crystal molecule orientation in the liquid crystal cell 3 is identified as "$\phi$". Therefore, the director of the exit side liquid crystal of the liquid crystal cell 3 is twisted at an angle $\phi$.

Incident light is applied along the Z axis (vertically to the X-Y plane).

When the liquid crystal 3 is disposed so that the director of the light incident side liquid crystal is parallel to the X axis, the Jones' matrix representing the polarizing action of the liquid crystal cell 3 is expressed by the following equation (1):

$$J_{LC} = ej\frac{\pi d}{\lambda}(ne' + no)\begin{bmatrix} a & b \\ -b^* & a^* \end{bmatrix}. \quad (1)$$

In this equation, a* and b* represent a conjugate complex number (imaginary part whose sign is reversed) of a and b, respectively.

In equation (1), a and b are:

$$a = \frac{1}{x}\sin\phi\sin(x\phi) + \cos\phi\cos(x\phi) + j\frac{u}{x}\cos\phi\sin(x\phi) \quad (2)$$

$$b = \frac{1}{x}\cos\phi\sin(x\phi) - \sin\phi\cos(x\phi) + j\frac{u}{x}\cos\phi\sin(x\phi),$$

and x, u and w are:

$$x = \sqrt{1 + u^2} \quad (3)$$

$$u = \frac{\pi d}{\lambda\phi}(ne' - no) = \frac{\pi d}{\lambda\phi}\left(\frac{ne}{\sqrt{1 + w\sin^2\theta s}} - no\right)$$

$$w = \left(\frac{ne}{no}\right)^2 - 1.$$

Here, ne is the refractive index of light (extraordinary light) having a polarization plane parallel to the major axes of the liquid crystal molecules, no is the refractive index of light (ordinary light) having a polarization plane vertical to the major axes of the liquid crystal molecules, $\lambda$ is the wavelength of the light emitted from the light source 1, $\theta$s is the pre-tilt angle (angle of tilt of the liquid crystal molecules from the substrate), and d is the thickness of the liquid crystal layer.

The phase factor $\exp[j(\pi d/\lambda)(ne'+no)]$ in equation (1), which is not important in this case, will be omitted in the description below.

Electric field (polarization) components Ex and Ey, in the directions of the X and Y axes, of the light having transmitted by the liquid crystal cell 3 are expressed by a matrix such as the following equation (4):

$$\begin{bmatrix} Ex \\ Ey \end{bmatrix} = \begin{bmatrix} \cos\alpha & -\sin\alpha \\ \sin\alpha & \cos\alpha \end{bmatrix}\begin{bmatrix} a & b \\ -b^* & a^* \end{bmatrix}\begin{bmatrix} \cos\alpha & \sin\alpha \\ -\sin\alpha & \cos\alpha \end{bmatrix}\begin{bmatrix} 0 \\ 1 \end{bmatrix}. \quad (4)$$

In equation (4), a and b are defined as:

$a = a1 + ja2$ $b = b1 + jb2$ (5).

From equation (2), a1, a2, b1 and b2 are expressed by the following equations (6):

$$a1 = \frac{1}{x}\sin\phi\sin(x\phi) + \cos\phi\cos(x\phi) \quad (6)$$

$$a2 = \frac{u}{x}\cos\phi\sin(x\phi)$$

$$b1 = \frac{1}{x}\cos\phi\sin(x\phi) - \sin\phi\cos(x\phi)$$

$$b2 = \frac{u}{x}\sin\phi\cos(x\phi).$$

From the product of the matrix of equation (4), the electric field components Ex and Ey in the directions of the X and Y axes are expressed by the following equations (7):

$Ex = b1 + j(a2\sin 2\alpha + b2\cos 2\alpha)$ $Ey = a1 + j(-a2\cos 2\alpha + b2\sin 2\alpha)$ (7).

Therefore, for light transmitted by the liquid crystal cell 3, Stokes parameters S0, S1, S2 and S3 which represent the condition of polarization, are expressed by the following equations (8):

$$S0 = ExEx^* + EyEy^* \quad (8)$$
$$= a1^2 + a2^2 + b1^2 + b2^2 = 1$$
$$S1 = ExEx^* - EyEy^*$$
$$= b1^2 - a1^2 - a2^2\cos 4\alpha + b2^2\cos 4\alpha + 2a2b2\cos 4\alpha$$
$$S2 = ExEy^* + Ex^*Ey$$
$$= 2a1b1 + (b2^2 - a2^2)\sin 4\alpha - 2a2b2\cos 4\alpha$$
$$S3 = j[ExEy^* - Ex^*Ey]$$
$$= 2b1(b2\sin 2\alpha - a2\cos 2\alpha) - 2a1(a2\sin 2\alpha + b2\cos 2\alpha).$$

S0 is normally 1 and for completely polarized light, $S0^2 = S1^2 + S2^2 + S3^2$.

Figure 3:
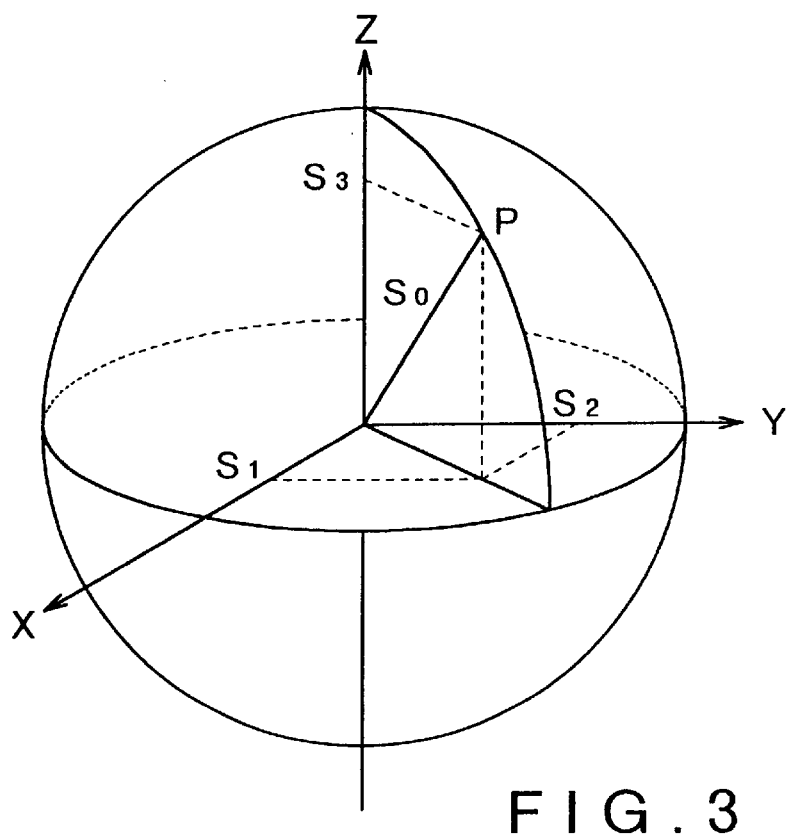
FIG. 3 is a view of a Poincare sphere.

The Stokes parameters (S0 to S3) represent a position P on the spherical surface of a Poincare sphere as shown in FIG. 3. Therefore, the condition of polarization is determined based upon the position on the spherical surface of the Poincare sphere.

In this method, the Stokes parameters (S0 to S3) are functions of a1, a2, b1, b2 and the angle $\alpha$ between the director of the light incident side liquid crystal and the X axis as shown in equations (8). Also, a1, a2, b1 and b2 are functions of the twist angle $\phi$ and u (i.e. the thickness d of the liquid crystal layer) as shown in equations (6).

However, two pairs of the Stokes parameters S1, S2 and S3 are independent parameters.

Therefore, when $\alpha$ is known, the twist angle $\phi$ and u (i.e. the thickness d of the liquid crystal layer) may be determined by measuring the values of two of the Stokes parameters S1, S2 and S3.

Figure 4:
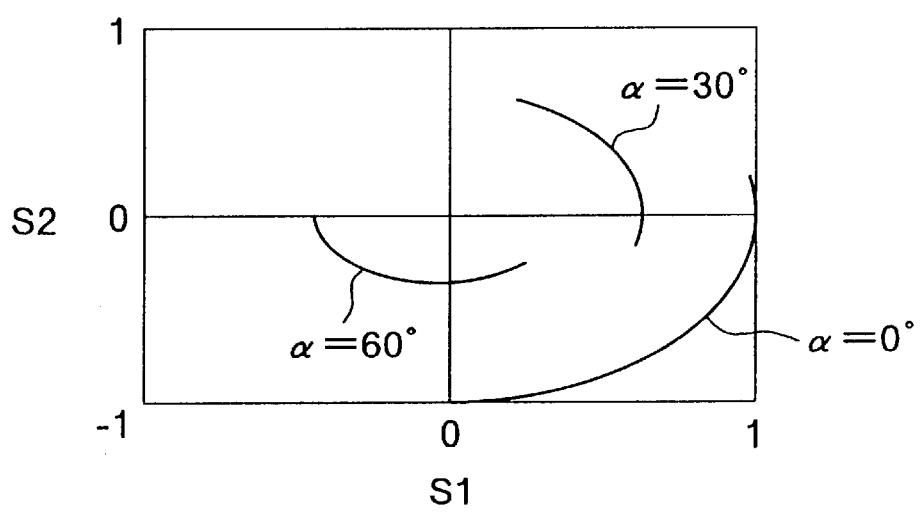
FIG. 4 is a view showing a relationship among Stokes parameters, the thickness of a liquid crystal layer and the angle of the twist of liquid crystal molecule orientation, etc.

A relationship between the Stokes parameters and $\alpha$, $\phi$ and d is shown in FIG. 4.

FIG. 4 shows the condition of variation of the Stokes parameters S1 and S2 when (1) $\phi$ is varied between 40 degrees and 90 degrees for the case in which $\alpha$ is set at 0 degrees, at 30 degrees and at 60 degrees (2) when K15 is used as the liquid crystal material, (3) light with a wavelength of 632.8 nm is applied to the liquid crystal cell and (4) the thickness of the liquid crystal layer is 10 µm.

Since the relationship between the Stokes parameters S1 and S2, and the twist angle $\phi$ varies according to the value of $\alpha$ as shown in FIG. 4, the influence of errors from determining the Stokes parameters on the accuracy for determining the twist angle $\phi$ can be reduced by selecting the value of $\alpha$.

Next, a method will be described for measuring the Stokes parameters and determining the twist angle $\phi$ and the thickness of the liquid crystal layer by use of the liquid crystal cell parameter detecting apparatus shown in FIG. 1.

First, the polarization direction of the polarizing plate 4 interposed between the liquid crystal cell 3 and the photodetector 6 is set in the direction of the X axis and an output Ix of the photodetector 6 at that time is measured.

Second, the polarization direction of the polarizing plate 4 is set in the direction of the Y axis and an output Iy of the photodetector 6 at that time is measured.

Third, the polarization direction of the polarizing plate 4 is set at 45 degrees to the X and Y axes and an output I45 of the photodetector 6 at that time is measured.

Fourth, with the polarization direction of the polarizing plate being set at 45 degrees to the X and Y axes, the quarter wavelength plate 5 is interposed between the polarizing plate 4 and the liquid crystal cell 3 so that its axial direction is tilted at 45 degrees to the polarization direction of the polarizing plate 4 (i.e., so that its axial direction is in the direction of the Y axis) and an output Iq45 of the photodetector 6 at that time is measured.

Expressing the Stokes parameters in terms of the measurement values Ix, Iy, I45 and Iq45, results in the following equations (9):

$$S0=(Ix+Iy)/(Ix+Iy)=1$$
$$S1=(Ix-Iy)/(Ix+Iy)$$
$$S2=[2I45-(Ix+Iy)]/(Ix+Iy)$$
$$S3=-[2Iq45-(Ix+Iy)]/(Ix+Iy) \quad (9).$$

Here, (Ix+Iy) is the value of the transmitted light intensity. The Stokes parameters shown in equations (9) are normalized by (Ix+Iy).

Therefore, by measuring Ix, Iy, I45 and Iq45, the Stokes parameters S1, S2 and S3 are obtained based on equations (9). The twist angle $\phi$ and u (i.e. the thickness d of the liquid crystal layer) can be determined from equations (8) and equations (6), etc.

When two pairs of the Stokes parameters S1 and S2 are measured, the measurement of Iq45 may be omitted. In this case, the quarter wavelength plate 5 is unnecessary and the structure of the measuring apparatus is simplified.

While the case in which a is known has been described, when $\alpha$ is unknown, the value of a can be obtained, for example, by rotating the polarizing plate 2 or the liquid crystal cell 3 and measuring Ix, Iy, I45 and Iq45 for different values of $\alpha$.

The value of $\alpha$ also may be obtained by another method.

Since S0 equals 1 and $S1^2+S2^2+S3^2$ equals 1, as is a characteristic of the Stokes parameters, this relationship may be used in order to reduce measurement errors.

That is, $S1^2+S2^2+S3^2$ does not equal 1 if there is a measurement error in the measurement values Ix, Iy, I45 and Iq45, etc. However, a position on the spherical surface of the Poincare sphere closest to the position on the Poincare sphere corresponding to the Stokes parameters obtained from the measurement values is determined and the Stokes parameters of that position are used instead. This method reduces measurement errors.

The table in FIG. 5 shows data from the determination of the thickness of the liquid crystal layer and the angle of twist of liquid crystal molecule orientation by use of the liquid crystal parameter detecting method according to the present invention.

(Sample 1)

For a liquid crystal cell in which the orientation film is a polyvinyl alcohol (PVA) film applied by spin coating PVA onto a glass substrate coated with a transparent conductive film, the substrate is rubbed in one direction after a heat treatment to orient the liquid crystal molecules, two substrates are then placed one on top of the other with a glass fiber spacer therebetween and the nematic liquid crystal E7 is sealed in. The thickness of the liquid crystal layer and the angle of twist were manufactured to be 25 µm and 30 degrees, respectively.

The Stokes parameters for the sample 1 were measured with the measuring apparatus shown in FIG. 1 and the obtained values were S1=0.696, S2=0.634 and S3=0.331. Then, based on these measured Stokes parameters, the thickness d of the liquid crystal layer and the angle $\phi$ of the twist of liquid crystal molecule orientation were determined to be d=25.32 µm and $\phi$=29.79 degrees.

(Sample 2)

For a liquid crystal cell using nematic liquid crystal E7, the thickness of the liquid crystal layer and the angle of twist were manufactured to be 25 μm and 85 degrees, respectively.

For sample 2, the measured values were S1=−0.158, S2=−0.873 and S3=0.460, and d=24.85 μm and φ=85.97 degrees.

(Sample 3)

For a liquid crystal cell using nematic liquid crystal K15, the thickness of the liquid crystal layer and the angle of twist were manufactured to be 5 μm and 85 degrees, respectively.

For sample 3, the measured values were S1=0.265, S2=0.534 and S3=−0.807, and d=4.87 μm and d=83.85 degrees.

As described above, according to the present invention, because the thickness of the liquid crystal layer and the angle of twist of liquid crystal molecule orientation are determined based upon Stokes parameters, the structure of the measuring apparatus is simplified and the measurement requires only a short time.

Specifically, because it is only necessary to rotate the polarizing plate 4 shown in FIG. 1 so that its direction of polarization is at 0 degrees, at 45 degrees and at 90 degrees and to insert the quarter wavelength plate 5, expensive equipment and complicated control apparatus are unnecessary and the measurement requires only a short time. In addition, since it is only necessary to measure the light intensity at each time, the measurement accuracy is high compared with previously known methods in which the capacitance and the optical phase difference are measured.

While the Stokes parameters are measured by use of the measuring apparatus shown in FIG. 1 in the above-described embodiment, the measuring apparatus for measuring the Stokes parameters is not limited thereto, and various measuring apparatus may be used.

As described above, by using a method of determining a parameter of a liquid crystal cell according to claim 1, liquid crystal parameters, such as the thickness of the liquid crystal layer and the angle of the twist of liquid crystal molecule orientation, are accurately measured in a short time with a simple apparatus.

What is claimed is:

1. A method of determining a parameter of a liquid crystal display cell, comprising the steps of:

measuring intensity of light signals by a photo detector, the light signals are incident to the liquid crystal cell and are transmitted from the liquid crystal cell;

calculating Stokes parameters of the liquid crystal cell from the output of the photo detector; and determining the parameter of the liquid crystal cell from the measured Stokes parameters, the parameter being selected from the group consisting of a thickness of the liquid crystal cell (d) and an angle of twist of liquid crystal molecule orientation within the liquid crystal cell (φ).

2. A method as in claim 1, wherein the step of measuring the intensity of the light signals that are incident to and are transmitted from the crystal cell, comprises the steps of:

interposing a polarizing plate between the liquid crystal cell and the photo detector in a direction of an X axis and measuring polarized light intensity (Ix) transmitted by the polarizing plate along the X axis;

interposing the polarizing plate between the liquid crystal cell and the photo detector in a direction of a Y axis and measuring polarized light intensity (Iy) transmitted by the polarizing plate along the Y axis;

interposing the polarizing plate between the liquid crystal cell and the photo detector in a direction of a 45° angle between the X and Y axes and measuring polarized light intensity (I45) transmitted by the polarizing plate along the 45° angle.

3. A method as in claim 2, wherein Stokes parameters are calculated from the following equations:

$S0=(Ix+Iy)/(Ix+Iy)=1$;

$S1=(Ix-Iy)/(Ix+Iy)$; and $S2=[2(I45)-(Ix+Iy)]/(Ix+Iy)$.

4. A method as in claim 3, wherein d is calculated from S0, S1 and S2.

5. A method as in claim 3, wherein φ is calculated from S0, S1 and S2.

6. A method as in claim 3, wherein d and φ are calculated from S0, S1 and S2.

7. A method as in claim 2, wherein the step of measuring Stokes parameters of the liquid crystal cell further comprises the steps of:

interposing a quarter wavelength plate between the polarizing plate, while interposing the polarizing plate between the liquid crystal cell and the photo detector in a direction of a 45° angle between the X and Y axes, wherein the quarter wavelength plate has a polarizing direction and the polarizing plate is interposed such that the polarizing direction of the quarter wavelength plate is at a 45° angle to the polarizing direction of the polarizing plate; and measuring polarized light intensity (Iq45) transmitted by the polarizing plate.

8. A method as in claim 1, wherein Stokes parameters are calculated from the following equations:

$S0=(Ix+Iy)/(Ix+Iy)=1$;

$S1=(Ix-Iy)/(Ix+Iy)$;

$S2=[2(I45)-(Ix+Iy)]/(Ix+Iy)$; and $S3=-[2(Iq45)-(Ix+Iy)]/(Ix+Iy)$.

9. A method as in claim 8, wherein d is calculated from S0, S1, S2 and S3.

10. A method as in claim 8, wherein φ is calculated from S0, S1, S2 and S3.

11. A method as in claim 8, wherein d and φ are calculated from S0, S1, S2 and S3.

12. An apparatus for determining a parameter of a liquid crystal cell, comprising:

a light source;

a first polarizing plate, the light source incident to the polarizing plate which provides a polarized light source;

a second polarizing plate, wherein the liquid crystal cell is disposed between the first and second polarizing plates such that the polarized light is incident to the liquid crystal cell and light transmitted from the liquid crystal cell is incident to the second polarizing plate;

a photo detector for measuring light intensity transmitted from the second polarizing plate and outputting transmitted light intensity values; and a processor, wherein the processor calculates the Stokes parameters based upon the transmitted light intensity values, and generates the parameter of the liquid crystal cell from the calculated Stokes parameters, the parameter being selected from the group consisting of a thickness of the liquid crystal cell (d) and an angle of twist of liquid crystal molecule orientation within the liquid crystal cell ($\phi$).

13. An apparatus as in claim 12, wherein the first polarizing plate is fixed in position.

14. An apparatus as in claim 13, wherein the second polarizing plate is settable in positions that are (1) in a direction of an X axis, (2) in a direction of a Y axis and (3) in a direction of that is 45° between the X and Y axes.

15. An apparatus as in claim 14, wherein the processor generates Stokes parameters based upon three transmitted light intensity values, Ix, Iy and I45, wherein Ix is generated when the second polarizing plate is in the direction of the X axis, Iy is generated when the second polarizing plate is in the direction of the Y axis and I45 is generated when the second polarizing plate is in the direction that is 45° between the X and Y axis.

16. An apparatus as in claim 15, wherein the processor generates three Stokes parameters according to the equations:

$$S0=(Ix+Iy)/(Ix+Iy)=1;$$

$$S1=(Ix-Iy)/(Ix+Iy); \text{ and}$$

$$S2=[2(I45)-(Ix+Iy)]/(Ix+Iy).$$

17. An apparatus as in claim 16, wherein the processor generates the parameter from Ix, Iy and I45 and the parameter is selected from the group consisting of a thickness of the liquid crystal cell (d) and an angle of twist of liquid crystal molecule orientation within the liquid crystal cell ($\phi$).

18. An apparatus as in claim 15, further comprising a quarter wavelength plate inserted between the liquid crystal cell and the second polarizing plate, wherein a fourth transmitted light value, Iq45, is generated when the second polarizing plate is the direction that is 45° between the X and Y axis.

19. An apparatus as in claim 18, wherein the processor generates four Stokes parameters according to the equations:

$$S0=(Ix+Iy)/(Ix+Iy)=1;$$

$$S1=(Ix-Iy)/(Ix+Iy);$$

$$S2=[2(I45)-(Ix+Iy)]/(Ix+Iy); \text{ and}$$

$$S3=-[2(Iq45)-(Ix+Iy)]/(Ix+Iy).$$

20. An apparatus as in claim 19, wherein the processor generates the parameter from Ix, Iy, I45 and Iq45 and the parameter is selected from the group consisting of a thickness of the liquid crystal cell (d) and an angle of twist of liquid crystal molecule orientation within the liquid crystal cell ($\phi$).

* * * * *